(12) United States Patent
Trombley

(10) Patent No.: US 10,105,264 B2
(45) Date of Patent: Oct. 23, 2018

(54) EAR CLEANING DEVICE

(71) Applicant: Frederick W. Trombley, Simi Valley, CA (US)

(72) Inventor: Frederick W. Trombley, Simi Valley, CA (US)

( * ) Notice: Subject to any disclaimer, the term of this patent is extended or adjusted under 35 U.S.C. 154(b) by 216 days.

(21) Appl. No.: 15/273,299

(22) Filed: Sep. 22, 2016

(65) Prior Publication Data
US 2018/0078421 A1 Mar. 22, 2018

(51) Int. Cl.
*A61F 11/00* (2006.01)

(52) U.S. Cl.
CPC .................. *A61F 11/006* (2013.01)

(58) Field of Classification Search
CPC .. A61F 11/006; A61F 13/38; A61B 2017/246; A61B 90/70; A61B 2090/701
See application file for complete search history.

(56) References Cited

U.S. PATENT DOCUMENTS

| | | | | |
|---|---|---|---|---|
| 4,820,259 A * | 4/1989 | Stevens | ................... | A61F 11/00 604/1 |
| 5,107,861 A | 4/1992 | Narboni | | |
| 5,715,850 A | 2/1998 | Markgraaf | | |
| 5,766,143 A * | 6/1998 | Bennett | ................. | A61F 13/385 15/118 |
| D432,239 S | 10/2000 | Shimizu | | |
| 6,695,802 B1 * | 2/2004 | Thompson | ............ | A61F 11/006 604/1 |
| 6,776,786 B2 | 8/2004 | Kim | | |
| 6,939,360 B2 | 9/2005 | Crespo | | |
| D631,957 S * | 2/2011 | Perez | ..................... | A61F 11/006 D24/119 |
| 8,551,031 B2 | 10/2013 | Edme et al. | | |
| 9,549,854 B1 * | 1/2017 | Crespo | ................... | A61F 11/006 |
| 2002/0004664 A1 * | 1/2002 | Gerstein | ............... | A61F 11/006 606/162 |
| 2003/0233063 A1 * | 12/2003 | Nakatani | .................. | A61F 13/38 604/2 |
| 2005/0076461 A1 * | 4/2005 | Tsaur | ....................... | A61F 13/38 15/209.1 |
| 2006/0085018 A1 | 4/2006 | Clevenger | | |
| 2011/0301572 A1 * | 12/2011 | Vlodaver | ................ | A61F 11/00 604/514 |
| 2012/0296355 A1 * | 11/2012 | Burres | ................... | A61F 11/006 606/162 |
| 2016/0302973 A1 * | 10/2016 | Kraitzer | ................ | A61M 31/00 |

FOREIGN PATENT DOCUMENTS

EP 0556432 2/1992

* cited by examiner

*Primary Examiner* — Jonathan Miles

(57) ABSTRACT

An ear cleaning device for more facile and healthier ear wax removal includes a tube and a pair of cups. Each cup is coupled singly to and extends from a respective opposing end of the tube. Each cup comprises an annular wall that extends between a bottom and a top to define an internal space. The bottom is positioned adjacent to the tube. The top is open. The tube is configured to be grasped by the digits of a hand of a user. The cups are configured to insert into an ear of the user. Debris, such as wax, that positioned on a wall of the ear canal of the ear is collected upon an external surface of a cup as the cup is rotated within the ear canal. Debris that is positioned proximate to the wall of the ear canal is collected in the internal space of the cup.

13 Claims, 1 Drawing Sheet

EAR CLEANING DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIE THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to ear cleaning devices and more particularly pertains to a new ear cleaning device for more facile and healthier ear wax removal.

BRIEF SUMMARY OF THE INVENTION

An embodiment of the disclosure meets the needs presented above by generally comprising a tube and a pair of cups. Each cup is coupled singly to and extends from a respective opposing end of the tube. Each cup comprises an annular wall that extends between a bottom and a top to define an internal space. The bottom is positioned adjacent to the tube. The top is open. The cups are positioned on the tube such that the tube is configured to be grasped by the digits of a hand of a user. A respective cup is configured to insert into an ear of the user. Debris, such as wax, that positioned on a wall of the ear canal of the ear is collected upon an external surface of the respective cup as the respective cup is rotated within the ear canal. Debris that is positioned proximate to the wall of the ear canal is collected in the internal space of the respective cup.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will from the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
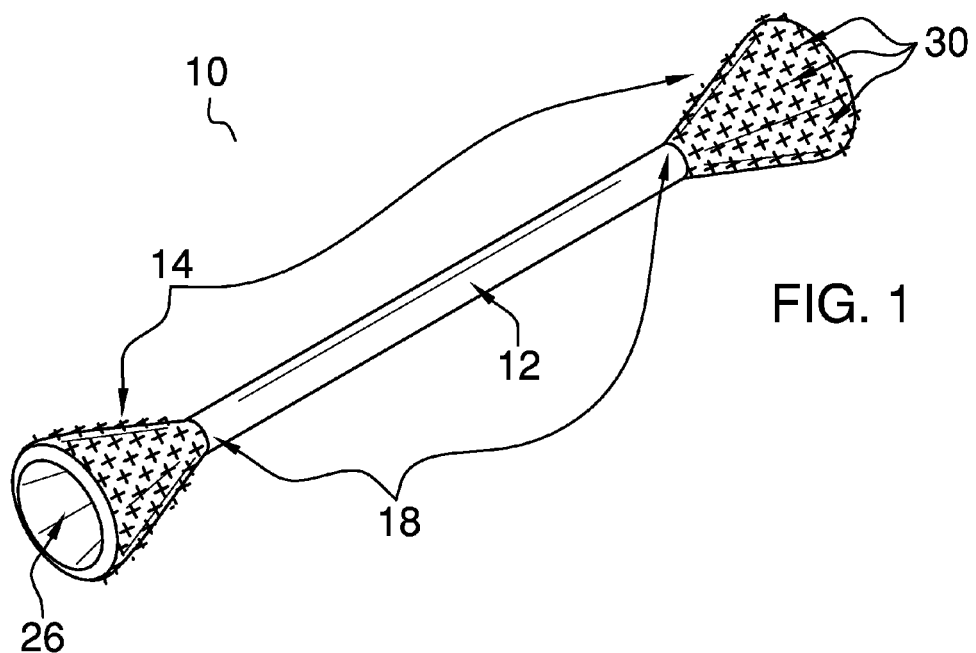
FIG. 1 is an isometric perspective view of an ear cleaning device according to an embodiment of the disclosure.
Figure 2:
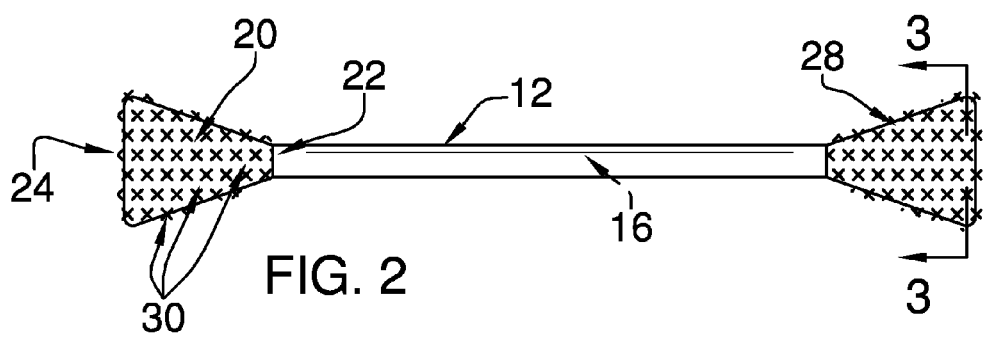
FIG. 2 is a side view of an embodiment of the disclosure.
Figure 3:
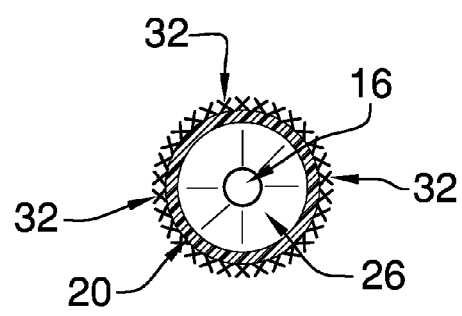
FIG. 3 is a cross-sectional view of an embodiment of the disclosure.

With reference now to the drawings, and in particular to FIGS. 1 through 3 thereof, a new ear cleaning device embodying the principles and concepts of an embodiment of the disclosure and generally designated by the reference numeral 10 will be described.

As best illustrated in FIGS. 1 through 3, the ear cleaning device 10 generally comprises a tube 12 and a pair of cups 14. In one embodiment, the tube 12 is substantially circularly shaped when viewed longitudinally. In another embodiment, the tube 12 is hollow and defines an interior space 16.

Each of the pair of cups 14 is coupled to and extends from a respective opposing end 18 of the tube 12. Each cup 14 comprises an annular wall 20 that extends between a bottom 22 and a top 24 of the cup 14, thus defining an internal space 26. The bottom 22 is positioned adjacent to the tube 12. The top 24 is open. The cups 14 are positioned on the tube 12 such that the tube 12 is configured to be grasped by the digits of a hand of a user. A respective cup 14 is configured to insert into an ear of the user. Debris, such as wax, that is positioned on a wall of an ear canal of the ear is collected upon an external surface 28 of the respective cup 14 as the respective cup 14 is rotated within the ear canal. Debris that is positioned proximate to the wall in the ear canal is collected in the internal space 26 of the respective cup 14.

In one embodiment, the bottom 22 is open so that the internal space 26 of the cup 14 is fluidically coupled to the interior space 16 of the tube 12. In another embodiment, the top 24 and the bottom 22 are circular. The top 24 is dimensionally larger than the bottom 22 such that the cup 14 is substantially conically shaped.

In one embodiment, the cups 14 are substantially transparent. In another embodiment, the cups 14 comprise plastic. In yet another embodiment, the cups 14 comprise soft plastic.

A plurality of bristles 30 is coupled to and extends from the external surface 28 of each cup 14. The bristles 30 are positioned on the cups 14 such that the bristles 30 are configured for collecting debris, such as wax that is positioned on the wall of the ear canal of the ear, as the cup 14 is rotated within the ear canal. In one embodiment, the bristles 30 are positioned in pairs of two bristles 32. In another embodiment, each of the bristles 30 that comprises the pair of two bristles 32 extends transversely from the external surface 28, such that each pair of two bristles 32 is X-shaped.

In one embodiment, the bristles 30 are substantially transparent. In another embodiment, the bristles 30 comprise plastic. In yet another embodiment, the bristles 30 comprise soft plastic.

In use, the cups 14 are positioned on the tube 12 such that the tube 12 is configured to be grasped by the digits of a hand of a user. A respective cup 14 is configured to insert into an ear of the user. The bristles 30 are positioned on the cups 14 such that the bristles 30 are configured for collecting debris, such as wax that is positioned on a wall of the ear canal of the ear, as the cup 14 is rotated within the ear canal. Debris that is positioned proximate to the wall in the ear canal is collected in the internal space 26 of the respective cup 14.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An ear cleaning device comprising:
    a tube;
    a pair of cups coupled singly to and extending from opposing ends of said tube, each said cup comprising an annular wall extending between a bottom and a top of said cup defining an internal space of said cup, said bottom being positioned adjacent to said tube, said top being open; and
    wherein said cups are positioned on said tube such that said tube is configured for grasping by the digits of a hand of a user, such that a respective said cup is configured for insertion into an ear of the user, wherein debris, such as wax, positioned on a wall of the ear canal of the ear is collected upon an external surface of said respective said cup as said respective said cup is rotated within the ear canal, and wherein debris positioned proximate to the wall in the ear canal is collected in said internal space of said respective said cup; and
    wherein said top and said bottom being circular, said top having a larger diameter than said bottom, such that said cup is substantially conically shaped.

2. The device of claim 1, further including said tube being substantially circularly shaped when viewed longitudinally.

3. The device of claim 1, further including said tube being hollow defining an interior space.

4. The device of claim 3, further including said bottom being open such that said internal space of said cup is fluidically coupled to said interior space of said tube.

5. The device of claim 1, further including said cups being substantially transparent.

6. The device of claim 1, further including said cups comprising plastic.

7. The device of claim 6, further including said cups comprising soft plastic.

8. The device of claim 1, further including a plurality of bristles coupled to and extending from said external surface of each said cup, wherein said bristles are positioned on said cups such that said bristles are configured for collecting debris, such as wax, positioned in the ear of the user as said cup is rotated within the ear of the user.

9. The device of claim 8, further including said bristles being positioned in pairs of two said bristles extending transversely from said external surface, such that each of said pairs of two said bristles is X-shaped.

10. The device of claim 8, further including said bristles being substantially transparent.

11. The device of claim 8, further including said bristles comprising plastic.

12. The device of claim 11, further including said bristles comprising soft plastic.

13. An ear cleaning device comprising:
    a tube, said tube being substantially circularly shaped when viewed longitudinally, said tube being hollow defining an interior space;
    a pair of cups coupled singly to and extending from opposing ends of said tube, each said cup comprising an annular wall extending between a bottom and a top of said cup defining an internal space said cup, said bottom being positioned adjacent to said tube, said top being open, wherein said cups are positioned on said tube such that said tube is configured for grasping by the digits of a hand of a user, such that a respective said cup is configured for insertion into an ear of the user, wherein debris, such as wax, positioned on a wall of an ear canal of the ear is collected upon an external surface of said respective said cup as said respective said cup is rotated within the ear canal, and wherein debris positioned proximate to the wall of the ear canal is collected in said internal space of said respective said cup, said bottom being open such that said internal space of said cup is fluidically coupled to said interior space of said tube, said top and said bottom being circular, said top being dimensionally larger than said bottom, such that said cup is substantially conically shaped, said cups being substantially transparent, said cups comprising soft plastic;
    a plurality of bristles coupled to and extending from said external surface of each said cup, wherein said bristles are positioned on said cups such that said bristles are configured for collecting debris, such as wax, positioned on a wall of the ear canal of the ear as said cup is rotated within the ear canal, said bristles being positioned in pairs of two said bristles extending transversely from said external surface, such that each of said pairs of two said bristles is X-shaped, said bristles being substantially transparent, said bristles comprising soft plastic.

* * * * *